United States Patent
Im et al.

(10) Patent No.: US 10,745,426 B2
(45) Date of Patent: Aug. 18, 2020

(54) LIGAND COMPOUND, ORGANIC CHROMIUM COMPOUND, CATALYST SYSTEM FOR OLEFIN OLIGOMERIZATION, AND METHOD FOR OLIGOMERIZING OLEFIN USING SAME

(71) Applicant: LG Chem, Ltd., Seoul (KR)

(72) Inventors: Seul Ki Im, Daejeon (KR); Yong Ho Lee, Daejeon (KR); Ki Soo Lee, Daejeon (KR); Eun Ji Shin, Daejeon (KR); Jin Young Park, Daejeon (KR); Seok Pil Sa, Daejeon (KR); Yoon Ki Hong, Daejeon (KR)

(73) Assignee: LG Chem, Ltd. (KR)

( * ) Notice: Subject to any disclaimer, the term of this patent is extended or adjusted under 35 U.S.C. 154(b) by 95 days.

(21) Appl. No.: 15/765,613

(22) PCT Filed: Nov. 25, 2016

(86) PCT No.: PCT/KR2016/013720
§ 371 (c)(1),
(2) Date: Apr. 3, 2018

(87) PCT Pub. No.: WO2017/095085
PCT Pub. Date: Jun. 8, 2017

(65) Prior Publication Data
US 2019/0077816 A1    Mar. 14, 2019

(30) Foreign Application Priority Data

Dec. 4, 2015 (KR) ........................ 10-2015-0172686

(51) Int. Cl.
| | |
|---|---|
| *C07F 9/50* | (2006.01) |
| *C07C 11/107* | (2006.01) |
| *C07F 9/02* | (2006.01) |
| *C07F 9/70* | (2006.01) |
| *C07F 11/00* | (2006.01) |
| *C07F 9/90* | (2006.01) |
| *C08F 4/69* | (2006.01) |
| *C08F 10/00* | (2006.01) |
| *B01J 31/18* | (2006.01) |
| *B01J 31/34* | (2006.01) |
| *C08F 10/02* | (2006.01) |

(52) U.S. Cl.
CPC .......... *C07F 9/5068* (2013.01); *B01J 31/189* (2013.01); *B01J 31/34* (2013.01); *C07C 11/107* (2013.01); *C07F 9/02* (2013.01); *C07F 9/50* (2013.01); *C07F 9/70* (2013.01); *C07F 9/90* (2013.01); *C07F 11/00* (2013.01); *C08F 4/69* (2013.01); *C08F 10/00* (2013.01); *B01J 2231/20* (2013.01); *C08F 4/69043* (2013.01); *C08F 10/02* (2013.01)

(58) Field of Classification Search
None
See application file for complete search history.

(56) References Cited

U.S. PATENT DOCUMENTS

| | | | |
|---|---|---|---|
| 7,141,633 B2 | 11/2006 | Wass | |
| 7,786,336 B2 | 8/2010 | Zhang et al. | |
| 7,829,749 B2 | 11/2010 | Gao et al. | |
| 7,910,670 B2 | 3/2011 | Knudsen et al. | |
| 7,964,763 B2 | 6/2011 | Dixon et al. | |
| 8,067,654 B2 | 11/2011 | Bercaw et al. | |
| 8,309,779 B2 | 11/2012 | Han et al. | |
| 9,040,445 B2 | 5/2015 | Eastham et al. | |
| 9,040,750 B2 | 5/2015 | Gao et al. | |
| 2002/0128501 A1 | 9/2002 | Zhang | |
| 2011/0282016 A1 | 11/2011 | Carter et al. | |
| 2012/0172645 A1 | 7/2012 | Sydora | |
| 2015/0152200 A1 | 6/2015 | Nanton et al. | |
| 2015/0361118 A1 | 12/2015 | Lee et al. | |
| 2016/0122371 A1 | 5/2016 | Lee et al. | |

FOREIGN PATENT DOCUMENTS

| | | |
|---|---|---|
| CN | 103285926 A | 9/2013 |
| JP | 2004513950 A | 5/2004 |
| KR | 20130142151 A | 12/2013 |
| KR | 20150006474 A | 1/2015 |
| KR | 20150037581 A | 4/2015 |
| KR | 20150058049 A | 5/2015 |
| WO | 2005123884 A2 | 12/2005 |
| WO | 2007057458 A1 | 5/2007 |
| WO | 2008004986 A1 | 1/2008 |

OTHER PUBLICATIONS

Suttil et al. Catal. Sci. Technol., 4, 2574-2588 (Year: 2014).*
Elowe et al., Nitrogen-Lined Diphosphine Ligands with Ethers Attached to Nitrogen for Chromium-Catalyzed Ethylene Tri- and Tetramerizations, Organometallics, vol. 25, pp. 5255-5260, Sep. 30, 2006.
ESSR for EP Application No. 16870981.4 dated Aug. 2, 2018.
Search report from International Application No. PCT/KR2016/013720, dated Feb. 28, 2017.
Weng, Zhigiang, et al., "Cromium(III) catalysed ethylene tetramerization promoted by bis(phosphino)amines with an N-functionalized pendant." Dalton Transactions, vol. 32, Aug. 28, 2007, pp. 3493-3498.
Fliedel, Christophe, et al., "Janus Microspheres for Visual Assessment of Molecular Interconnects." Chemistry-A European Journal, vol. 20 (2014) (Received: Sep. 13, 2013, Published online on Dec. 30, 2013), pp. 1263-1266.

(Continued)

*Primary Examiner* — Yun Qian
(74) *Attorney, Agent, or Firm* — Lerner, David, Littenberg, Krumholz & Mentlik, LLP

(57) ABSTRACT

The present invention relates to a ligand compound, a catalyst system for olefin oligomerization and a method for oligomerizing an olefin using same. The catalyst system for olefin oligomerization according to the present invention exhibits high selectivity to 1-hexene or 1-octene while having excellent catalytic activity, thus enabling more efficient preparation of alpha-olefins.

1 Claim, No Drawings

(56) References Cited

OTHER PUBLICATIONS

Suttil, et al., "A survey of pendant donor-functionalised (N,O) phosphine ligands for Cr-catalysed ethylene tri- and tetramerisation." Catalysis Science & Technology, vol. 4 (Received Apr. 11, 2014; Accepted May 8, 2014), pp. 2574-2588.

Killian, Esna, et al., "The use of bis(diphenylphosphino)amines with N-aryl functionalities in selective ethylene tri- and tetramerisation." Journal of Molecular Catalysis A: Chemical 270 (Received Jan. 11, 2007; Accepted Jan. 30, 2007; Available online Feb. 6, 2007), pp. 214-218.

Kayan, Cezmi, et al., "Synthesis and reactivity of bis(diphenylphosphino)amine ligands and their appliction in Suzuki cross-coupling readctions." Inorganica Chimica Acta, vol. 385 (Received Jul. 27, 2011; Accepted Jan. 26, 2012; Available online Feb. 1, 2012), pp. 164-169.

* cited by examiner

LIGAND COMPOUND, ORGANIC CHROMIUM COMPOUND, CATALYST SYSTEM FOR OLEFIN OLIGOMERIZATION, AND METHOD FOR OLIGOMERIZING OLEFIN USING SAME

CROSS-REFERENCE TO RELATED APPLICATION(S)

The present application is a national phase entry under 35 U.S.C. § 371 of International Application No. PCT/KR2016/013720 filed on Nov. 25, 2016, which claims priority from Korean Patent Application No. 10-2015-0172686 filed on Dec. 4, 2015, the disclosures of which are incorporated herein by reference.

TECHNICAL FIELD

The present invention relates to a ligand compound, an organic chromium compound, a catalyst system for olefin oligomerization containing the ligand compound and the organic chromium compound, and a method for oligomerizing an olefin using same.

BACKGROUND ART

Linear alpha-olefins such as 1-hexene, 1-octene, and like are used in detergents, lubricants, plasticizers, and so on, and in particular, they are frequently used as comonomers for controlling the density of a polymer during the preparation of linear low-density polyethylene (LLDPE).

Such linear alpha-olefins were mainly produced through a Shell Higher Olefin Process. However, since the above process synthesizes alpha-olefins of various lengths simultaneously in accordance with Schultz-Flory distribution, there was an inconvenience of requiring an additional separation step in order.

To solve these problems, a method of selectively synthesizing 1-hexene through a trimerization reaction of ethylene or a method of selectively synthesizing 1-octene through a tetramerization reaction of ethylene has been proposed. Further, various studies have been conducted on a catalyst system enabling such selective oligomerization of ethylene.

DETAILED DESCRIPTION OF THE INVENTION

Technical Problem

It is an object of the present invention to provide a novel ligand compound capable of exhibiting high catalytic activity and selectivity in olefin oligomerization reaction.

It is another object of the present invention to provide a novel organic chromium compound capable of exhibiting high catalytic activity and selectivity in olefin oligomerization reaction.

It is still another object of the present invention to provide a catalyst system for olefin oligomerization containing the ligand compound or the organic chromium compound.

It is a further object of the present invention to provide a method for oligomerizing olefins using the catalyst system.

Technical Solution

One embodiment of the present invention provides a ligand compound represented by the following chemical formula 1 or 2.

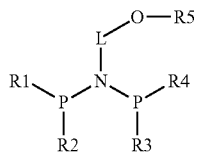

[Chemical Formula 1]

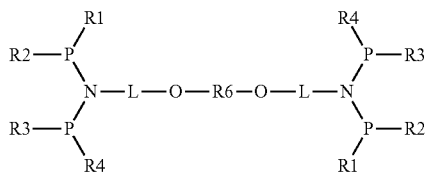

[Chemical Formula 2]

in Chemical Formulas 1 and 2,

N is a nitrogen atom, P is a phosphorus atom, O is an oxygen atom,

L is a hydrocarbylene having 2 to 10 carbon atoms connecting N and O, and the number of carbons in the shortest chain connecting N and O is 2 to 4, R1 to R4 are equal to or different from each other and each independently represent a hydrocarbyl group or a heterohydrocarbyl group having 2 to 20 carbon atoms;

R5 is an alkyl group having 1 to 10 carbon atoms, an aryl group having 6 to 15 carbon atoms, an alkylsilyl group having 1 to 10 carbon atoms, an arylsilyl group having 6 to 15 carbon atoms, a silylalkyl group having 1 to 10 carbon atoms, or a silyl aryl group having 6 to 15 carbon atoms or an alkylarylsilyl group having 6 to 15 carbon atoms, and R6 is an alkylene having 1 to 10 carbon atoms, an arylene having 6 to 15 carbon atoms, an alkylsilylene having 1 to 10 carbon atoms, an arylsilylene having 6 to 15 carbon atoms, a silylalkylene having 1 to 10 carbon atoms, a silylarylene having 6 to 15 carbon atoms, or an alkylarylsilylene having 6 to 15 carbon atoms.

Another embodiment of the present invention provides an organic chromium compound comprising chromium (Cr) to which the ligand compound is coordinated.

Still another embodiment of the present invention provides a catalyst system for olefin oligomerization comprising i) a source of chromium, the above-described ligand compound, and a cocatalyst, or ii) the above-described organic chromium compound, and a cocatalyst.

A further embodiment of the present invention provides a method for oligomerizing an olefin comprising the step of performing an oligomerization reaction of olefins in the presence of the above-described catalyst system to form alpha-olefins.

Advantageous Effects

A catalyst system for olefin oligomerization according to the present invention exhibits high selectivity to 1-hexene or 1-octene while having excellent catalytic activity, thus enabling more efficient preparation of alpha-olefins.

DETAILED DESCRIPTION OF THE EMBODIMENTS

Hereinafter, the ligand compound, the organic chromium compound, the catalyst system for olefin oligomerization, and the method for oligomerizing an olefin using the same according to the embodiments of the present invention will be described in more detail.

Technical terms used in the present specification are only for mentioning specific embodiments, and they are not intended to restrict the present invention. The singular expressions used herein may include plural expressions unless the context explicitly indicate otherwise. The terms such as "including", "comprising", or "having" as used herein are intended to embody specific features, numbers, steps, components, and/or combinations thereof, and does not exclude existence or addition of other specific features, numbers, steps, components, and/or combinations thereof.

The invention can make various modifications and take various forms, and thus specific embodiments are illustrated and described in detail below. It should be understood, however, that the invention is not intended to be limited to any particular disclosure form, but includes all modifications, equivalents and alternatives falling within the spirit and scope of the invention.

Further, in the present specification, "catalyst system" means what can be obtained as the catalyst composition having activity by mixing three components including a source of chromium, a ligand compound, and a cocatalyst, or alternatively two components of an organic chromium compound and a cocatalyst, at the same time or in an arbitrary order. Said three components or two components of the catalyst system may be mixed in the presence or absence of a solvent and a monomer, and it may be used in the form of being supported or unsupported.

In the present specification, the hydrocarbyl group means a monovalent group formed by removing one hydrogen atom from a hydrocarbon, and the heterohydrocarbyl group means a monovalent group formed by removing one hydrogen atom from a hydrocarbon containing a hetero atom. The hydrocarbylene means a divalent linking group formed by removing two hydrogen atoms from a hydrocarbon.

In the respective functional groups. "functional group is substituted" means a state in which one or more hydrogen atoms are further removed from a hydrocarbon and a different functional group or heteroatom is substituted.

According to one aspect of the present invention, there is provided a ligand compound represented by the following chemical formula 1 or 2.

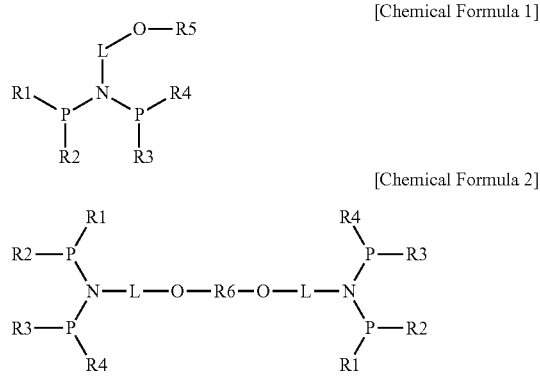

[Chemical Formula 1]

[Chemical Formula 2]

in Chemical Formulas 1 and 2,

N is a nitrogen atom, P is a phosphorus atom, O is an oxygen atom,

L is a hydrocarbylene having 2 to 10 carbon atoms connecting N and O, and the number of carbons in the shortest chain connecting N and O is 2 to 4, R1 to R4 are equal to or different from each other and each independently represents a hydrocarbyl group or a heterohydrocarbyl group having 2 to 20 carbon atoms;

R5 is an alkyl group having 1 to 10 carbon atoms, an aryl group having 6 to 15 carbon atoms, an alkylsilyl group having 1 to 10 carbon atoms, an arylsilyl group having 6 to 15 carbon atoms, a silylalkyl group having 1 to 10 carbon atoms, or a silyl aryl group having 6 to 15 carbon atoms or an alkylarylsilyl group having 6 to 15 carbon atoms, and R6 is an alkylene having 1 to 10 carbon atoms, an arylene having 6 to 15 carbon atoms, an alkylsilylene having 1 to 10 carbon atoms, an arylsilylene having 6 to 15 carbon atoms, a silylalkylene having 1 to 10 carbon atoms, a silylarylene having 6 to 15 carbon atoms, or an alkylarylsilylene having 6 to 15 carbon atoms.

As the results of successive experiments of the present inventors, it has been found that, when the ligand compound is applied to a catalyst system for olefin oligomerization, it exhibits excellent selectivity to 1-hexene or 1-octene while exhibiting excellent catalytic activity, thus enabling more efficient preparation of alpha-olefins.

According to one embodiment of the invention, the ligand compound includes a diphosphino aminyl moiety in the molecule, wherein the nitrogen of the aminyl moiety is connected via a hydrocarbylene linker to a substituent comprising an oxygen atom.

Due to the structural features including ether bonds or silyl ether bonds as described above, the ligand compound can be applied to a catalyst system for olefin oligomerization catalyst system and thus exhibit high oligomerization reaction activity, particularly high selectivity to 1-hexene or 1-actene.

This can be seen to be attributed to the interaction between respective adjacent chromium active sites. Particularly, the oxygen atom and the silicon atom connected to the diphosphinoaminyl group via the linker have an electric effect and a steric hindrance effect and thus the electron density increases at phosphorus(P) atom and nitrogen(N) atom included in the diphosphinoiminyl group, or the unshared electron pair of the oxygen atom is directly coordinated to chromium, so that the electrical and steric properties of the entire ligand compound can be changed.

Consequently, the bond between the ligand and the chromium atom is changed, and so the structure of the catalyst can be more stabilized. Further, the energy of the transition state, that is, the activation energy of the reaction, is changed, by allowing the formation of alpha-olefins with higher activity and selectivity, compared to conventional metallacycloheptane or metallacyclononane forms, and it becomes possible to further reduce the amount of by-products such as high molecular weight solid alpha-olefins such as PE wax.

Furthermore, the amount of the 1-hexene isomer which greatly affects the product even in a small amount in the oligomerization reaction can be greatly reduced and, incidentally, separation may be unnecessary due to increase of 1-hexene and decrease of 1-hexene isomer, thereby bringing about an energy saving effect.

In Chemical Formula 1, R1 to R4 are equal to or different from each other, and each independently represents a hydrocarbyl group or a heterohydrocarbyl group.

As a non-limiting example, R1 to R4 are each independently a substituted or unsubstituted alkyl group having 1 to 10 carbon atoms, a substituted or unsubstituted cycloalkyl group having 4 to 10 carbon atoms, a substituted or unsubstituted aryl group having 6 to 15 carbon atoms, a substituted or unsubstituted arylalkyl group having 7 to 15 carbon atoms, or a substituted or unsubstituted alkoxy group having 1 to 10 carbon atoms. Here, at least one hydrogen contained in the alkyl group, cycloalkyl group, aryl group, arylalkyl group, and alkoxy group may be substituted with an alkyl group having 1 to 10 carbon atoms, an alkoxy group having 1 to 10 carbon atoms, a halogen atom, or a cyano group.

Preferably, the R1 to R4 may be each independently methyl, ethyl, propyl, propenyl, propynyl, butyl, cyclohexyl, 2-methylcyclohexyl, 2-ethylcyclohexyl, 2-isopropylcyclohexyl, benzyl, phenyl, tolyl, xylyl, o-methylphenyl, o-ethylphenyl, o-isopropylphenyl, o-t-butylphenyl, o-methoxyphenyl, o-isopropoxyphenyl, m-methylphenyl, m-ethylphenyl, m-isopropylphenyl, m-t-butylphenyl, m-methoxyphenyl, m-isopropoxyphenyl, p-methylphenyl, p-ethylphenyl, p-isopropylphenyl, p-t-butylphenyl, p-p-methoxyphenyl, p-isopropoxyphenyl, cumyl, mesityl, biphenyl, naphthyl, anthracenyl, methoxy, ethoxy, phenoxy, tolyloxy, dimethylamino, thiomethyl, or trimethylsilyl groups.

R5 is a substituent connected to the diphosphinoaminyl moiety through an oxygen atom and a linker L, and may be an alkyl group having 1 to 10 carbon atoms, an aryl group having 6 to 15 carbon atoms, an alkylsilyl group having 1 to 10 carbon atoms, an arylsilyl group having 6 to 15 carbon atoms, a silylalkyl group having 1 to 10 carbon atoms, a silylaryl group having 6 to 15 carbon atoms, or an alkylarylsilyl group having 6 to 15 carbon atoms, more preferably an alkylsilyl group having 1 to 10 carbon atoms, an arylsilyl group having 6 to 15 carbon atoms, or an alkylarylsilyl group having 6 to 15 carbon atoms.

Chemical Formula 2 means that the above-mentioned ligand compound forms a dimer form. In this case, R6 is a linker for connecting the respective monomer ligand compounds, and may be an alkylene having 1 to 10 carbon atoms, an arylene having 6 to 15 carbons, an alkylsilylene having 1 to 10 carbons, an arylsilylene having 6 to 15 carbons, an silylalkylene having 1 to 10 carbon atoms, a silylarylene having 6 to 15 carbon atoms, or an alkylarylsilylene having 6 to 15 carbon atoms, preferably an alkylsilylene having 1 to 10 carbon atoms, an arylsilylenes having 6 to 15 carbon atoms, or an alkylarylsilylene having 6 to 15 carbon atoms.

In addition to the above-mentioned electrical effects and steric hindrance effects, the R5 and R6 are easy to increase the electron density of diphosphinoaminyl moiety due to a silyl ether linkage, and also it is very easy to provide an unshared electron pair directly to a chromium atom through a three-dimensional structure.

According to another aspect of the present invention, there is provided an organic chrome compound comprising chromium (Cr) to which a ligand compound represented by the following Chemical Formula 1 or 2 is coordinated.

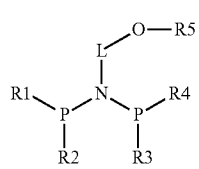

[Chemical Formula 1]

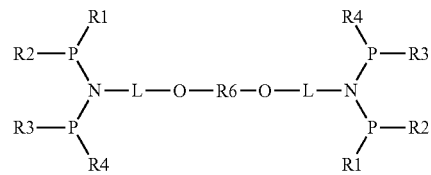

[Chemical Formula 2]

in Chemical Formulas 1 and 2,

N is a nitrogen atom, P is a phosphorus atom, O is an oxygen atom,

L is a hydrocarbylene having 2 to 10 carbon atoms connecting N and O, and the number of carbons in the shortest chain connecting N and O is 2 to 4, R1 to R4 are equal to or different from each other and each independently represents a hydrocarbyl group or a heterohydrocarbyl group having 2 to 20 carbon atoms;

R5 is an alkyl group having 1 to 10 carbon atoms, an aryl group having 6 to 15 carbon atoms, an alkylsilyl group having 1 to 10 carbon atoms, an arylsilyl group having 6 to 15 carbon atoms, a silylalkyl group having 1 to 10 carbon atoms, or a silyl aryl group having 6 to 15 carbon atoms or an alkylarylsilyl group having 6 to 15 carbon atoms, and R6 is an alkylene having 1 to 10 carbon atoms, an arylene having 6 to 15 carbon atoms, an alkylsilylene having 1 to 10 carbon atoms, an arylsilylene having 6 to 15 carbon atoms, a silylalkylene having 1 to 10 carbon atoms, a silylarylene having 6 to 15 carbon atoms, or an alkylarylsilylene having 6 to 15 carbon atoms.

Details are the same as disclosed in the ligand compound part.

The organic chromium compound may be a chromium complex compound of the above-mentioned ligand compound, and may have a structure in which the chromium of the source of chromium forms a coordinate bond with an unshared electron pair of a nitrogen atom of the group represented by Chemical Formula 1. Such organic chromium compound can be applied to catalyst systems for the oligomerization reaction of olefins and thus exhibit excellent catalytic activity and high selectivity to 1-hexene or 1-octene.

According to an embodiment of he present invention, it is preferable that the organic chromium compound is in a form in which at least one unshared electron pair among N, P, and O in the ligand compound is coordinated to a chromium atom. That is, in addition to the phosphorus atom or nitrogen atom of the diphosphinoaminyl moiety, the oxygen atom of the substituent can provide an unshared electron pair to the chromium atom, as described above. Particularly, a tridentated state in which three pairs of the unshared electron pair are coordinated may be desirable.

Meanwhile, according to another aspect of the present invention, there is provided a catalyst system for olefin oligomerization i) comprising a source of chromium, the above-described ligand compound and a cocatalyst; or ii) comprising the above-described organic chromium compound, and a cocatalyst.

That is, according to one embodiment of the invention, the catalyst system for olefin oligomerization may be i) a tricomponent catalyst system including a source of chromium, the above-described ligand compound, and a cocatalyst, or ii) a bicomponent catalyst system including the above-described organic chromium compound and a cocatalyst.

Details and specific examples about the ligand compound and the organic chromium compound are the same as disclosed above.

In the catalyst system, the source of chromium may be an organic or inorganic chromium compound having an oxidation state of chromium of 0 to 6, and examples thereof include a chromium metal, or a compound in which any organic or inorganic radical is bonded to chromium. Here, the organic radicals may be alkyl, alkoxy, ester, ketone, amido, carboxylate radicals having 1 to 20 carbon atoms per radical, and the inorganic radicals may be halides, sulfates, oxides, and the like.

Preferably, the source of chromium is a compound which can exhibit a high activity for oligomerization of olefins and which is easily usable and available. The source of chromium may be at least one compound selected from the group consisting of chromium (III) acetylacetonate, chromium (III) chloride tetrahydrofuran, chromium (III) 2-ethylhexanoate, chromium (III) acetate, chromium (III) butyrate, chromium (III) pentanoate, chromium (III) laurate, chromium (III) tris(2,2,6,6-tetramethyl-3,5-heptiedionate), and chromium (III) stearate.

Preferably, the cocatalyst is an organic metal compound including a Group 13 metal, and any cocatalyst can be used without particular limitation as long as it is any compound which can be generally used for polymerizing an olefin in the presence of a catalyst of a transition metal compound.

For example, the cocatalyst may be at least one compound selected from the group consisting of compounds represented by the following chemical formulas 3 to 5:

—[Al(Rx)-O]$_c$—      [Chemical Formula 3]

in Chemical Formula 3, Al is aluminum,

Rx is equal to or different from each other and each independently represent a halogen radical, a hydrocarbyl radical having 1 to 20 carbon atoms, or a hydrocarbyl radical having 1 to 20 carbon atoms substituted with a halogen, and c is an integer of 2 or more, D(Ry)$_3$      [Chemical Formula 4]

in Chemical Formula 4, D is aluminum or boron, Ry is a hydrocarbyl having 1 to 20 carbon atoms or a hydrocarbyl having 1 to 20 carbon atoms substituted with halogen,

[L-H]$^+$[Q(E)$_4$]$^-$      [Chemical Formula 5]

in Chemical Formula 5,

L is a neutral Lewis base, [L-H]$^+$ is a Bronsted acid, Q is boron or aluminum of a +3 oxidation state, and each E is independently a $C_6$-$C_{20}$ aryl group or a $C_1$-$C_{20}$ alkyl group of which at least one hydrogen is substituted or unsubstituted with a halogen, a $C_1$-$C_{20}$ hydrocarbyl, an alkoxy functional group, or a phenoxy functional group.

According to one embodiment, the compound represented by Chemical Formula 2 may be an alkyl aluminoxane such as methyl aluminoxane, ethyl aluminoxane, isobutyl aluminoxane, butyl aluminoxane, and the like.

According to one embodiment, the compound represented by Chemical Formula 3 may be trimethylaluminum, triethylaluminum, triisobutylaluminum, tripropylaluminum, tributylaluminum, dimethylchloroaluminum, dimethylisobutylaluminum, dimethylethylaluminum, diethylchloroaluminum, triisopropylaluminum, tri-s-butylaluminum, tricyclopentylaluminum, tripentylaluminum, triisopentylaluminum, trihexylaluminum, ethyldimethylaluminum, methyldiethylaluminum, triphenylaluminum, tri-p-tolylaluminum, dimethylaluminummethoxide, dimethylaluminu- methoxide, trimethylboron, triethylboron, triisobutylboron, tripropylboron, tributylboron, and so on.

Furthermore, according to one embodiment, the compound represented by Chemical Formula 4 may be triethylammonium tetraphenylborate, tributylammonium tetraphenylborate, trimethylammonium tetraphenylborate, tripropylammonium tetraphenylborate, trimethylammonium tetra(p-tolyl)borate, tripropylammonium tetra(p-tolyl)borate, triethylammonium tetra(o,p-dimethylphenyl)borate, trimethylammonium tetra(o,p-dimethylphenyl)borate, tributylammonium tetra(p-trifluoromethylphenyl)borate, trimethylammonium tetra(p-trifluoromethylphenyl)borate, tributylammonium tetrapentafluorophenylborate, N,N-diethylanilinium tetraphenylborate, N,N-diethylanilinium tetraphenylborate, N,N-diethylanilinium tetrapentafluorophenylborate, diethylammonium tetrapentafluorophenylborate, triphenylphosphonium tetraphenylborate, trimethylphosphonium tetraphenylborate, triethylammonium tetraphenylaluminum, tributylammonium tetraphenylaluminum, trimethylammonium tetraphenylaluminum, tripropylammonium tetraphenylaluminum, trimethylammonium tetra(p-tolyl)aluminum, tripropylammonium tetra(p-tolyl)aluminum, triethylammonium tetra(o,p-dimethylphenyl)aluminum, tributylammonium tetra(p-trifluoromethylphenyl)aluminum, trimethylammonium tetra(p-trifluoromethylphenyl)aluminum, tributylammonium tetrapentafluorophenylaluminum, N,N-diethylanilinium tetraphenylaluminum, N,N-diethylanilinium tetraphenylaluminum, N,N-diethylanilinium tetrapentafluorophenylaluminum, diethylammonium tetrapentafluorophenylaluminum, triphenylphosphonium tetraphenylaluminum, trimethylphosphonium tetraphenylaluminum, triphenylcarbonium tetraphenylborate, triphenylcarbonium tetraphenylaluminum, triphenylcarbonium tetra(p-trifluoromethylphenyl)borate, triphenylcarbonium tetrapentafluorophenylborate, and so on.

Moreover, as a non-limiting example, the cocatalyst may be an organic aluminum compound, an organic boron compound, an organic magnesium compound, an organic zinc compound, an organic lithium compound, or a mixture thereof. According to one embodiment, the cocatalyst is preferably an organic aluminum compound, more preferably at least one compound selected from the group consisting of trimethyl aluminum, triethyl aluminum, triisopropyl aluminum, triisobutyl aluminum, ethylaluminum sesquichloride, diethylaluminum chloride, ethyl aluminum dichloride, methyl aluminoxane, and modified methyl aluminoxane.

Meanwhile, the content ratio of the components constituting the catalyst system may be determined by considering the catalytic activity and the selectivity to linear alpha-olefins. According to one embodiment, when the catalyst system is a tricomponent catalyst system, it is preferable that the mole ratio of diphosphino aminyl moiety of the ligand compound: the source of chromium: the cocatalyst is controlled to be about 1:1:1 to 10:1:10,000, or about 1:1:100 to 5:1:3,000. Further, when the catalyst system is a bicomponent catalyst system, it is preferable that the mole ratio of diphosphino aminyl moiety of the organic chromium compound to the cocatalyst is controlled to be 1:1 to 1:10,000, or 1:1 to 1:5,000, or 1:1 to 1:3,000.

The components constituting the catalyst system may be added at the same time or in an arbitrary order in the presence or absence of a proper solvent and a monomer to act as an active catalyst system. In this case, the proper solvent may be heptane, toluene, cyclohexane, mehtylcyclohexane, 1-hexene, 1-octene, diethylether, tetrahydrofuran, acetonitrile, dichloromethane, chloroform, chlorobenzene, methanol, acetone, and so on.

Further, according to an embodiment of the present invention, the catalyst system may further include a support. That is, the ligand compound of Chemical Formula 1 may be applied to the oligomerization of ethylene in the form of being supported on the support. The support may be metals, metal salts, metal oxides, or the like, which are commonly applied to a supported catalyst. By way of non-limiting examples, the support may be silica, silica-alumina, silica-magnesia, and the like, and may include oxides, carbonates, sulfates, nitrates of metals such as $Na_2O$, $K_2CO_3$, $BaSO_4$, and $Mg(NO_3)_2$.

Meanwhile, according to another aspect of the present invention, there is provided a method for oligamerizing an olefin, comprising the step of carrying out an oligomerization reaction of an olefin in the presence of the above-described catalyst system to form an alpha-olefin.

The method for oligomerizing an olefin according to the present invention may be carried out by using an olefin (for example, ethylene) as a raw material and applying the above-mentioned catalyst system and a common device and contact technology. By way of non-limiting examples, the oligomerization reaction of olefin may be carried out by a homogeneous liquid phase reaction in the presence or absence of an inert solvent, by a slurry reaction using the catalyst system that is partially or not totally dissolved, by a bulk reaction in which the alpha-olefin, the product, acts as a main medium, or by a gas phase reaction.

Further, the oligomerization reaction of olefin may be carried out in the presence of an inert solvent. By way of non-limiting examples, the inert solvent may be benzene, toluene, xylene, cumene, chlorobenzene, dichlorobenzene, heptane, cyclohexane, methylcyclohexane, methylcyclopentane, n-hexane, 1-hexene, 1-octene, and so on.

The oligomerization reaction of olefin may be carried out at a temperature of about 0 to about 200° C., or about 0 to about 150° C., or about 30 to about 100° C., or about 50 to about 100° C. Furthermore, the reaction may be carried out at a pressure of about 15 to about 3,000 psig, or about 15 to about 1,500 psig, or about 15 to about 1,000 psig.

Hereinafter, the action and effect of the present invention will be described in more detail by way of specific Examples. However, these Examples are given for illustrative purposes only, and the scope of the invention is not intended to be limited by these Examples.

EXAMPLE

In the following, all reactions were performed using Schlenk technique or a glove box under argon. The synthesized ligands were analyzed by $^{31}P$ (500 MHz) NMR spectra using a Varian 500 MHz spectrometer. Shift was expressed in ppm, downfield from TMS, with a residual solvent peak as a reference. Phosphorous probe was calibrated with aqueous $H_3PO_4$.

Synthesis of Ligand Compound

Synthesis Example 1

Synthesis of

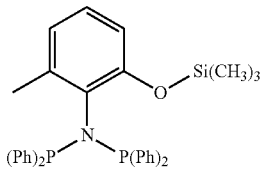

0.62 g (5 mmol) of 2-amino-3-methylphenol was weighed in a Schlenk flask in a glove box and taken out, to which 30 ml of tetrahydrofuran was added.

A reactor was prepared with acetone to which dry ice was added, and under this condition, 2.2 ml of 2.5 M n-BuLi was added dropwise, followed by stirring for 30 minutes. 0.63 ml (5 mmol) of chlorotrimethylsilane was slowly added dropwise thereto, and the mixture was stirred overnight.

After the solvent was removed under vacuum, the reaction mixture was dissolved in methyl-t-butyl ether, stirred and filtered with an air-free glass filter to remove triethylammonium chloride salt. The resultant was sampled and subjected to $^1$H-NMR measurement to confirm that a trimethylsilyl group was bonded due to hydrogen shift.

30 ml of dichloromethane was added dropwise thereto, and 2.79 ml (20 mmol) of triethylamine and 1.85 ml (10 mmol) of chlorodiphenylphosphine were sequentially, slowly added dropwise, and the reaction mixture was stirred overnight.

After the solvent was removed under vacuum the reaction mixture was dissolved in methyl-t-butyl ether, stirred and filtered with an air-free glass filter to remove triethylammonium chloride salt. The solvent was removed from the filtrate to obtain a target compound.

$^{31}P$ NMR (500 MHz, $CDCl_3$): 81.678 (s), 59.200 (s), 36.845 (m)

Synthesis Example 2

Synthesis of

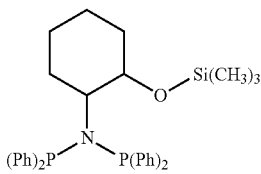

0.58 g (5 mmol) of 2-aminocyclohexanol was weighed in a Schlenk flask in a glove box and taken out, to which 30 ml of tetrahydrofuran was added.

A reactor was prepared with acetone to which dry ice was added, and under his condition, 2.2 ml of 2.5 M n-BuLi was added dropwise, followed by stirring for 30 minutes. 0.63 ml (5 mmol) of chlorotrimethylsilane was slowly added dropwise thereto, and the mixture was stirred overnight.

After the solvent was removed under vacuum, the reaction mixture was dissolved in methyl-t-butyl ether, stirred and filtered with an air-free glass filter to remove triethylammonium chloride salt. The resultant was sampled and subjected to $^1$H-NMR measurement to confirm that a trimethylsilyl group was bonded due to hydrogen shift.

30 ml of MC(methyl Chloride) was added dropwise thereto, and 2.79 ml (20 mmol) of triethylamine and 1.85 ml (10 mmol) of chlorodiphenylphosphine were sequentially, slowly added dropwise, and the reaction mixture was stirred overnight.

After the solvent was removed under vacuum, the reaction mixture was dissolved in methyl-t-butyl ether, stirred and filtered with an air-free glass filter to remove triethylammonium chloride salt. The solvent was removed from the filtrate to obtain a target compound.

$^{31}$P NMR (500 MHz, CDCl$_3$): 55.107 (m), 54.194 (m), 47.901 (m), 46.289 (m)

Synthesis Example 3

Synthesis of

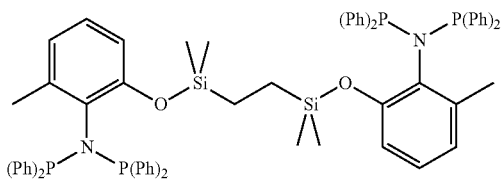

0.62 g (5 mmol) of 2-amino-3-methylphenol was weighed in a Schlenk flask in a glove box and taken out, to which 30 ml of tetrahydrofuran was added.

A reactor was prepared with acetone to which dry ice was added, and under his condition, 2.2 ml of 2.5 M n-BuLi was added dropwise, followed by stirring for 30 minutes. 0.54 ml (2.5 mmol) of 1,2-bis(chlorotrimethylsilyl) ethane was slowly added dropwise thereto, and the mixture was stirred overnight.

After the solvent was removed under vacuum, the reaction mixture was dissolved in methyl-t-butyl ether, stirred and filtered with an air-free glass filter to remove triethylammonium chloride salt. The resultant was sampled and subjected to $^1$H-NMR measurement to confirm that a silyl group was bonded due to hydrogen shift.

30 ml of MC was added dropwise thereto, and 2.79 ml (20 mmol) of triethylamine and 1.85 ml (10 mmol) of chlorodiphenylphosphine were sequentially, slowly added dropwise, and the reaction mixture was stirred overnight.

After the solvent was removed under vacuum, the reaction mixture was dissolved in rnethyl-t-butyl ether, stirred and filtered with an air-free glass filter to remove triethylammonium chloride salt. The solvent was removed from the filtrate to obtain a target compound.

$^{31}$P NMR (500 MHz, CDCl$_3$): 59.302 (m)

Synthesis Example 4

Synthesis of

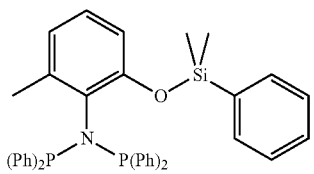

0.62 g (5 mmol) of 2-amino-3-methylphenol was weighed in a Schlenk flask in a glove box and taken out, to which 30 ml of tetrahydrofuran was added.

A reactor was prepared with acetone to which dry ice was added, and under his condition, 2.2 ml of 2.5 M n-BuLi was added dropwise, followed by stirring for 30 minutes. 0.84 ml (5 mmol) of hlorodimethylphenylsilane was slowly added dropwise thereto, and the mixture was stirred overnight.

After the solvent was removed under vacuum, the reaction mixture was dissolved in methyl-t-butyl ether, stirred and filtered with an air-free glass filter to remove triethylammonium chloride salt. The resultant was sampled and subjected to $^1$H-NMR measurement to confirm that a dimethylphenylsilyl group was bonded due to hydrogen shift.

30 ml of MC was added dropwise thereto, and 2.79 ml (20 mmol) of triethylamine and 1.85 ml (10 mmol) of chlorodiphenylphosphine were sequentially, slowly added dropwise, and the reaction mixture was stirred overnight.

After the solvent was removed under vacuum, the reaction mixture was dissolved in rnethyl-t-butyl ether, stirred and filtered with an air-free glass filter to remove triethylammonium chloride salt. The solvent was removed from the filtrate to obtain a target compound.

$^{31}$P NMR (500 MHz, CDCl$_3$): 59.618 (s)

Preparation of Catalyst System and Progress of Ethylene Oligomerization Reaction Examples 1 to 4

Chromium (III) acetylacetonate (17.5 mg, 0.05 mmol) and the ligand compound (0.025 mmol) according to Synthesis Example 1 to 4 were added to a flask under argon gas atmosphere, to which 10 ml of cyclohexane was added, and the mixture was stirred to prepare a 5 mM (based on Cr) catalyst solution.

A 600 mL Parr reactor was prepared, vacuum was applied at 180° C. for 2 hours, and then, the inside was replaced with argon, and the temperature was decreased to 60° C. After that, 140 g of metal-cyclohexane and 1.6 ml of MAO (8.6 wt % isoheptane solution, Al/Cr=1200) were injected, and 5 ml (2.5 pmol Cr) of 0.5 mM catalyst solution described above was injected. The reaction mixture was stirred at 500 rpm for 2 minutes, and then, a valve of an ethylene line adjusted to 60 bar was opened to fill the inside of the reactor with ethylene, followed by removing heat to 45° C., and stirring at 500 rpm for 15 minutes. The ethylene line valve was closed, the reactor was cooled to 0° C. with a dry ice/acetone bath, and then, non-reacted ethylene was slowly vented, and 0.5 ml of nonane(GC internal standard) was injected. After stirring for 10 seconds, 2 mL of the liquid part of the reactor was taken and quenched with water, the obtained organic part was filtered with a PTFE syringe filter to make a GC-FID sample. And, the distribution of liquid product was analyzed by GC. In addition, to the remaining reaction solution, 400 mL of ethanol/HCI (10 vol % of aqueous 12M HCI solution) was added, and the mixture was stirred and filtered, and the amount of solids was analyzed.

Thereafter, polyethylene wax obtained by drying overnight at 60° C. vacuum oven was added, and finally the product distribution was determined.

The results of Examples are summarized in table below.

TABLE 1

|  | Activity Ton/molCr/hr | C1-C6 wt % | C1-C8 wt % | C10-C40 wt % | Total wt % |
|---|---|---|---|---|---|
| Example 1 | 148 | 40.6 | 48.6 | 6.2 | 95.4 |
| Example 2 | 135 | 33.1 | 47.3 | 6.5 | 86.8 |
| Example 3 | 132 | 22.9 | 61.2 | 7.8 | 91.9 |
| Example 4 | 105 | 22.0 | 55.2 | 9.8 | 87.0 |

Referring to Table 1, it was confirmed that the catalyst system comprising the organic chromium compound of the present invention shows high selectivity to 1-hexene or 1-octene while having excellent catalytic activity in the olefin oligomerization reaction, thus enabling more efficient preparation of alpha-olefins.

The invention claimed is:

1. A ligand compound represented by the following chemical formulas,

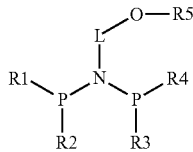

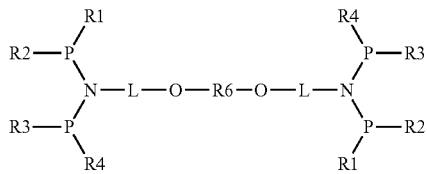

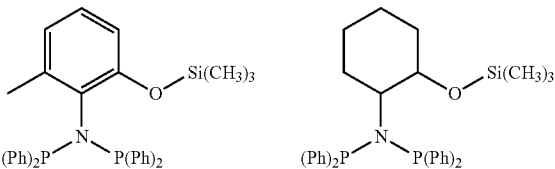

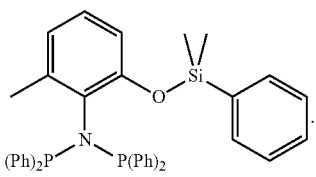

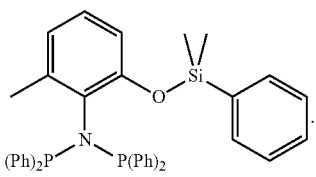

* * * * *

UNITED STATES PATENT AND TRADEMARK OFFICE
CERTIFICATE OF CORRECTION

PATENT NO.      : 10,745,426 B2  
APPLICATION NO. : 15/765613  
DATED           : August 18, 2020  
INVENTOR(S)     : Seul Ki Im et al.

Page 1 of 1

It is certified that error appears in the above-identified patent and that said Letters Patent is hereby corrected as shown below:

In the Claims

Column 13, after Line 20, the structure as follows should be deleted:

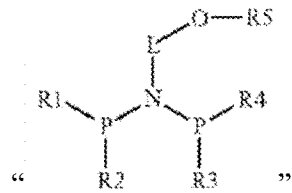

Column 14, Lines 1-10, the structure as follows should be deleted:

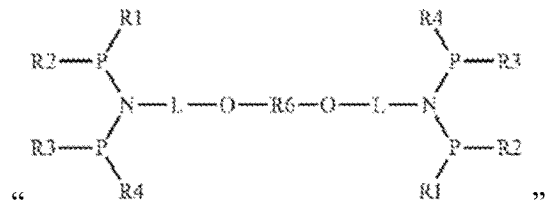

Signed and Sealed this  
Fifth Day of January, 2021

Andrei Iancu  
*Director of the United States Patent and Trademark Office*